(12) United States Patent
Mastorakis

(10) Patent No.: US 11,351,310 B2
(45) Date of Patent: Jun. 7, 2022

(54) INJECTION SYRINGE

(71) Applicant: NUMEDICO TECHNOLOGIES PTY LTD., Dulwich (AU)

(72) Inventor: Emmanuel Mastorakis, Monte-Carlo (MC)

(73) Assignee: Numedico Technologies Pty Ltd., Dulwich (AU)

( * ) Notice: Subject to any disclaimer, the term of this patent is extended or adjusted under 35 U.S.C. 154(b) by 262 days.

(21) Appl. No.: 16/314,288

(22) PCT Filed: May 17, 2017

(86) PCT No.: PCT/EP2017/061781
§ 371 (c)(1),
(2) Date: Dec. 28, 2018

(87) PCT Pub. No.: WO2018/001624
PCT Pub. Date: Jan. 4, 2018

(65) Prior Publication Data
US 2021/0038826 A1 Feb. 11, 2021

(30) Foreign Application Priority Data

Jun. 29, 2016 (FR) ..................................... 1656053

(51) Int. Cl.
*A61M 5/32* (2006.01)
(52) U.S. Cl.
CPC ..... *A61M 5/322* (2013.01); *A61M 2005/3224* (2013.01); *A61M 2209/086* (2013.01)
(58) Field of Classification Search
CPC .......... A61M 5/322; A61M 2005/3224; A61M 2005/323; A61M 2005/3231
See application file for complete search history.

(56) References Cited

U.S. PATENT DOCUMENTS

| 4,804,370 A | 2/1989 | Haber et al. |
| 5,328,475 A * | 7/1994 | Chen ..................... A61M 5/322 604/110 |

(Continued)

FOREIGN PATENT DOCUMENTS

| EP | 1244484 B1 | 11/2003 |
| WO | 9107198 | 5/1991 |

(Continued)

OTHER PUBLICATIONS

International Search Report from corresponding International Application No. PCT/EP2017/061781, dated Jul. 18, 2017, pp. 1-3, European Patent Office, Rijswijk, The Netherlands.

*Primary Examiner* — Laura A Bouchelle
(74) *Attorney, Agent, or Firm* — Bodman PLC

(57) ABSTRACT

A syringe provided with a body, a piston capable of sliding in the body, and an injection device comprising a needle oriented along a longitudinal axis and a casing removably secured to the body and carrying said needle. The casing comprising a plurality of flexible tabs, each provided with a stop. The piston comprising a docking system having a housing comprising a flange configured to hold the stops of the flexible tabs in the housing in an insertion position in which the tabs are inserted into the housing, the plurality of tabs in opposing areas around the longitudinal axis. The flange comprising bearing areas configured to be in contact with corresponding tabs in the insertion position. The tabs are configured to exert an elastic pressure on corresponding bearing areas in the insertion position, and the bearing areas are dissymmetrical relative to the longitudinal axis.

12 Claims, 3 Drawing Sheets

(56) References Cited

U.S. PATENT DOCUMENTS

| | | | | |
|---|---|---|---|---|
| 5,575,774 | A | * | 11/1996 | Chen ..................... A61M 5/322 604/110 |
| 6,669,666 | B2 | * | 12/2003 | Lu ......................... A61M 5/322 604/110 |
| 2004/0147876 | A1 | * | 7/2004 | Maggioni ............. A61M 5/322 604/110 |
| 2006/0253074 | A1 | * | 11/2006 | Thayer ................ A61M 5/3234 604/110 |
| 2008/0027381 | A1 | | 1/2008 | Smith et al. |

FOREIGN PATENT DOCUMENTS

| | | |
|---|---|---|
| WO | 2004014470 A1 | 2/2004 |
| WO | 2007123826 A2 | 11/2007 |
| WO | 2013067588 A1 | 5/2013 |

* cited by examiner

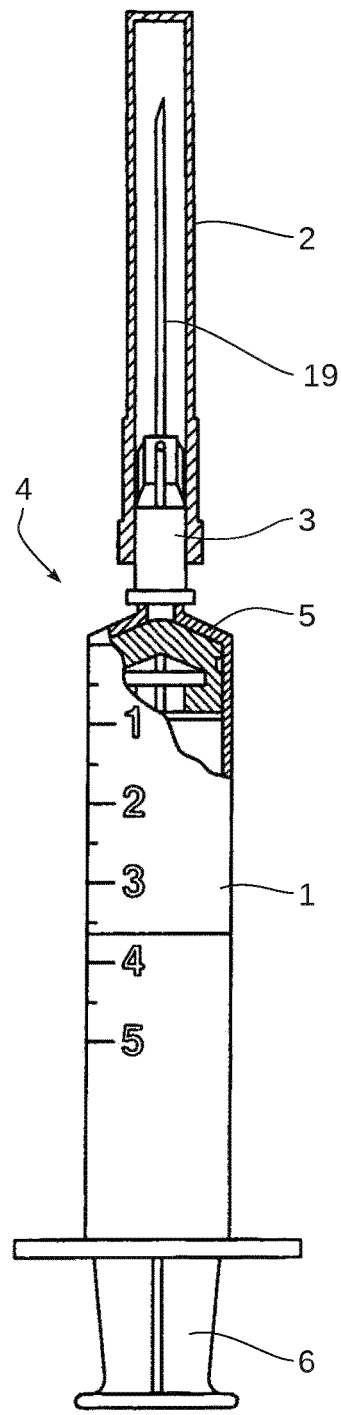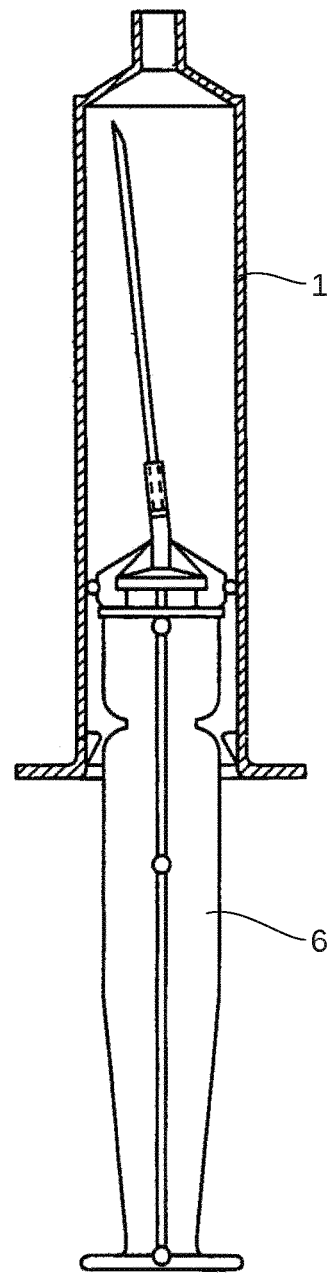
FIG 1
FIG 2

COUPE A-A

INJECTION SYRINGE

FIELD OF THE INVENTION

The present invention relates to an injection device and a syringe provided with such a device.

A preferred application is in the medical devices and accessories industry.

TECHNOLOGICAL BACKGROUND

In the medical field, injection devices using a needle are known, this term referring here to any pointed device allowing a fluid to pass therethrough towards the human or animal body in particular. In particular, such a device as a syringe comprising a body and a piston that can slide in the body is known from document WO 2004/014470 A1. In addition, to carry out the injection, the syringe includes an injection device attached to the head of the syringe body and provided with a needle. Such a device is illustrated in FIGS. 1 to 3. The device attached to the head of the syringe body comprises a part enabling it to be mounted on said body, as a mechanical interface and a part whereon the needle is assembled forming the casing receiving this needle. The casing and the interface are in contact. Nevertheless, according to this anteriority, the needle is retractable into the syringe body once the injection operations are completed. This provision provides greater safety of use to the medical device. To achieve this retraction, the casing carrying the needle is disconnected from the interface as shown in FIG. 2. The fact that the casing and the interface must move from a position where they are secured together and sealed to a position where they are disconnected raises sealing issues that are generally solved by separately applied O-rings.

The sealing techniques thus used seriously increase the complexity of the assembly of the devices and their costs.

A needle deflection system is known from US document U.S. Pat. No. 4,804,370 A1 in which the root of the needle, visible in FIG. 5, forms the deflection surface. The needle base is received in a symmetrical elastomer cavity.

US document A1 2008/027381 shows a single cooperation area (see FIG. 14) between a needle-bearing casing and a housing secured to the syringe piston. US document A1 2006/253074 discloses a cooperation equivalent to the previous publication between the piston and the casing.

Document WO A1 91/07198 shows a single, continuous tab in a plane transverse to the length of the syringe and provided with a stop capable of cooperating with a piston housing.

Document WO A2 2007/123826 also shows a cooperation between a single casing surface and a single surface of a piston housing.

The present invention makes it possible to remedy all or at least some of the drawbacks of the current techniques.

SUMMARY OF THE INVENTION

One aspect of the invention relates to a syringe provided with a body, a piston capable of sliding in the body, and an injection device comprising a needle oriented along a longitudinal axis and a casing removably secured to the body and carrying said needle, the casing comprising a plurality of flexible tabs each provided with a stop, the piston comprising a docking system provided with a housing that comprises a flange configured to hold the stops of the flexible tabs in the housing in an insertion position in which the tabs are inserted into the housing, the plurality of tabs comprising a first tab and a second tab situated in opposing areas around the longitudinal axis, the flange comprising a first bearing area and a second bearing area configured to be in contact respectively with the first tab and the second tab in the insertion position.

Advantageously, the first tab and the second tab are configured to exert an elastic pressure respectively on the first bearing area and the second bearing area in the insertion position, and the first bearing area and the second bearing area are dissymmetrical relative to the longitudinal axis.

Thus, the contact on the two bearing areas cannot be symmetrical around the longitudinal axis, the bearing forces are therefore not balanced, and this causes the casing and therefore the needle to tilt, so that the latter is permanently enclosed in the syringe body. The tilting is carried out efficiently without significant effort from the user because there is little resistance to the insertion sufficient to cause tilting. Advantageously but not restrictively, the tabs have a free distal end, and not joined together as is necessary in the case of a cavity bottom used for tilting the casing, so their flexibility can be chosen high.

It should be noted that there are several flexible tabs, which enables distinct elastic bearings to be provided on several places in the housing.

BRIEF DESCRIPTION OF THE FIGURES

Other characteristics, aims and advantages of the present invention will appear upon reading the following detailed description and referring to the appended drawings given as non-limiting examples and wherein:

FIG. 1 shows an overview of a syringe according to the state of the art described in document WO 2004/014470 A1;

FIG. 2 is a view of this state of the art showing a retracted position of the needle;

DETAILED DESCRIPTION

Figure 3:
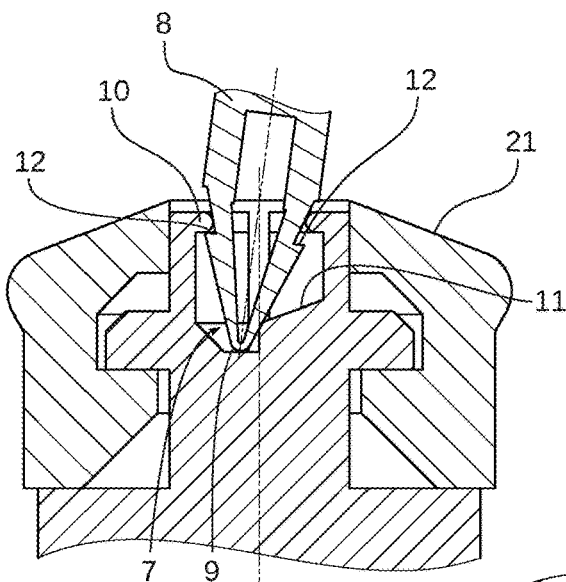
FIG. 3 is a cross-sectional view of a detail of the state of the art of FIGS. 1 and 2.

Prior to going into details relating to the preferred embodiments of the invention while referring more particularly to the drawings, other optional characteristics of the invention which may be implemented in any combination or alternately, are mentioned hereafter:

the first bearing area is further from the longitudinal axis than the second bearing area;

the first bearing area is on an annular flange and the second bearing area is a portion protruding beyond this flange towards the longitudinal axis;

the second bearing area is an angular sector of a ring;

the angular sector forms an angle greater than 30°;

the angular sector forms an angle of less than 90°;

the distance between two adjacent tabs is less than the width dimension of the second bearing area;

the plurality of tabs includes at least one pair of additional flexible tabs, with the tabs of the pair of tabs being situated in opposite areas about the longitudinal axis;

the first tab, the second tab and the additional tabs are uniformly distributed around the longitudinal axis;

the plurality of tabs includes only one pair of additional tabs;

the tabs of the plurality of tabs are symmetrical two by two relative to the longitudinal axis;

the distal ends of the tabs are disjointed.

For the proper understanding of the invention, the following definitions shall apply:

longitudinal axis 15: the long dimension of the needle, and may also be the long dimension of the syringe and/or the injection device and/or the piston when the needle is in position mounted on the syringe head and not retracted into the syringe body; generally speaking, the syringe body and/or the injection device and/or possibly any other part of the invention may have symmetry around the longitudinal direction of the assembly;

transverse, lateral or width mean a dimension oriented in a plane perpendicular to the longitudinal direction 15;

needle refers to any pointed device used to perform an injection function, in particular the injection of fluid into a human or animal body.

The device of the state of the art shown in FIG. 1 typically comprises a syringe body 1 here essentially cylindrical in shape and having a proximal end provided with a mouthpiece for receiving a piston 6 and an opposite distal end for receiving an injection device provided with a needle. At its distal end, the body 1 has a narrowed section head produced by a shoulder 5. Advantageously, the injection device is provided with a cap during storage. This is aimed at protecting the needle 19.

FIG. 2 shows the retraction functionality of the needle 19. To achieve this, the piston 6 has, at its distal end, a device allowing it to cooperate with a portion of the injection device whereon the needle 19 is mounted. Thus, when the piston 6 is brought sufficiently deep inside the body 1, it is docked to the secured part of the needle 19 and a subsequent sliding action of the piston 6 tending to pull it out of the body 1 enables the needle 19 to be retracted from the inside of the body 1 as shown in FIG. 2. Optionally, as shown in FIG. 2, a reduced cross-section of the piston 6 may provide a breakable area so as to break the piston and avoid excessive dimensions in this position. It is easy to understand that the needle 19 is thus protected, which offers greater safety than the most classical syringes.

According to the state of the art, a needle mounting possibility includes an interface 3 which is mounted at the head of the body 1 and which cooperates with a casing 8 provided with an inner channel receiving the needle 19. At its end opposite the reception area of the needle 19, the casing 8 comprises means of cooperation with the distal end of the piston 6. As a matter of fact, the needle is retracted by docking the lower end of its support (the casing) to the upper part of the piston so that a movement imparted to the piston causes the casing 8 and the needle 19 to move downward to a retracted position in the syringe body. FIG. 3 shows an insertion position in which the lower end of the casing 8 is inserted into a housing 7 and held in said housing by stops 12 which cooperate with a flange 10 bordering the upper end of the housing 7. The lower end of the casing 8 comprises two tabs with elastic bending deformation capacity (they are flexible) and are joined at their distal ends to form a point 9. Along its tabs, a narrowing of section produces a notch shape with a first edge forming the stop 12 and possibly a second edge forming an opposite stop. In the previous embodiment illustrated in FIG. 3, when inserting the tabs into the housing 7, a slugged bottom 11 of the housing deflects the point 9 so as to offset the casing 8 relative to the longitudinal axis of the piston 6. It is understood that the needle 19 is slugged relative to the piston to reach the position equivalent to the one shown in FIG. 2. In the situation of FIG. 3, the point 9 applies to the bottom of the housing 7 and the notched portions of the tabs are positioned opposite the flange 10 with a relative clearance; however, the stops 12 are configured not to enable the casing 8 to leave the housing 7, by holding same relative to the flange 10.

As a counterpoint to what is shown in FIGS. 1 to 3, FIGS. 4 to 8 show a non restrictive embodiment of the invention.

Figure 4:
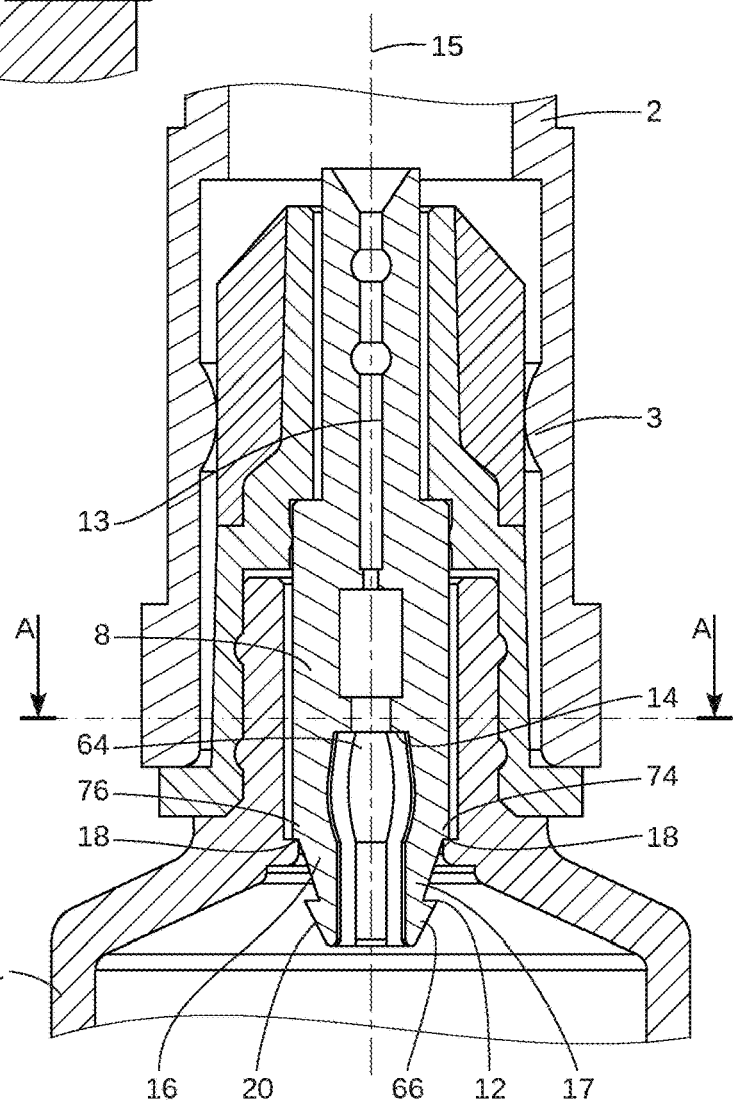
FIG. 4 is a cross-sectional view of one embodiment of the invention in a position where the casing of the insertion device is secured to the head of the syringe body.

FIG. 4 shows that the syringe, according to the invention, may have, as before, a body 1 with a head at which an injection device may be present, advantageously in relation to said head. A cap 2 is also visible. The injection device has an interface 3, one part of which is used for mounting on the head of the body 1 and another part for mounting the casing 8. The latter has a channel 13 for receiving the needle 19 and conducting the fluid through the syringe to the needle 19. A cylinder-to-cylinder press-fit is advantageously formed with the proximal end of the needle 19. Between its two ends, the casing 8 is secured to the interface 3. More precisely, a contact portion of the outer wall 12 of the casing 8 cooperates with an attachment portion of the inner wall 11 of the interface 3. This cooperation is advantageously removable so as to allow a retracted configuration of the device as shown in the example of FIG. 2. Thus, the securing of the casing 8 in the interface 3 can be configured to be overcome by a sufficient force, especially from a user during a phase of action on the piston, driving the casing 8 once it is docked at the end of the piston 6. At the very least, it is advantageous that the casing 8 is movable along a longitudinal axis 15 relative to the interface 3 when retracting the needle 19. Advantageously, sealing is provided between the interface 3 and the casing 8.

It should be noted, in the case shown in FIG. 4, that the casing 8 extends through the entire interface 3 so that it opens at a distal end on which a needle seat is formed and at a proximal end inside the syringe body 1. Throughout the casing 8, a channel 13 advantageously extends so as to enable a fluid to flow from the storage area inside the body 1 to the needle 19 for an injection. The fluid can then pass through the rest of the channel 13 until it exits out of the syringe. Advantageously, the casing 8 extends short of the proximal end of the interface 3 towards the body 1 and penetrates into the main volume of the body 1, below the shoulder 5. Thus, the distal end of the tabs described in greater details below protrudes into the body 1.

The components of the casing 8 and the interface are preferably each solid and come from a single piece of material, this material being preferably a plastic material.

FIG. 4 also shows that the casing 8 has tabs 16, 17. These tabs are advantageously flexible and are secured to the rest of the casing 8 at a base 14, for example as an end of a casing body 8. The tabs extend between the base 14 and a distal end of the tabs that is advantageously free, and the distal ends of the tabs are thus preferably disjointed. On the one hand, a central space that does not obstruct the passage of the injected liquid is cleared and, on the other hand, a significant deformation capacity in flexion of the tabs is obtained.

Each tab has, from its distal end, an insertion end 20 advantageously flared from said end so as to produce a preferably conical nose which facilitates the insertion thereof into the housing 7. Above the end 20, a stop 12 is present as before and can be obtained by narrowing the section. This section can be increased again a little higher so as to define the notched portion of the tabs and to create a stop area 18, which FIG. 4 shows can be used to create a stop part on a corresponding area of the syringe body. In the position shown in FIG. 4, the tabs thus produce a translation stop opposing the stop areas of the syringe body.

Figure 5:
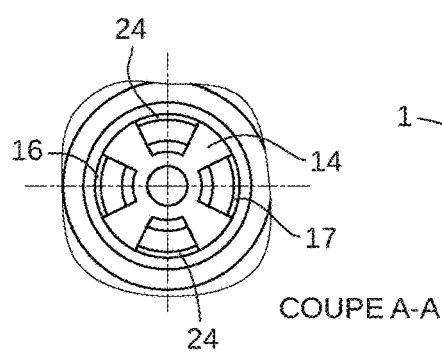
FIG. 5 is a cross-sectional view A-A of FIG. 4.

FIG. 5 also shows a detailed cross-sectional view transversally illustrating a possible arrangement of the tabs beyond the base 14. In particular, at least two tabs are present and have reference numbers 16 and 17. They are situated in opposite areas relative to the longitudinal axis 15. Preferably, the opposite areas are defined as two half spaces located on either side of a plane containing the longitudinal axis 15. Preferably, the tabs 16 and 17 are diametrically opposed around the longitudinal axis 15 and can be symmetrical relative to this axis. Preferably, the tabs are evenly spaced relative to the longitudinal axis 15 and are facing each other. Preferably, at least one pair of additional tabs 24 is also formed. Advantageously, the same relative position characteristics are found for the additional tabs 24 of each pair and the tabs 16, 17. Thus, the view on the right of FIG. 4 shows a pair of additional tabs 24. The tabs 16, 17, 24 are all identical in shape and size in this example and are uniformly distributed around the periphery of the base 14, with the latter being preferably circular. Thus, in this example, four tabs are present and the midpoints of their width are spaced 90° apart.

Figure 6:
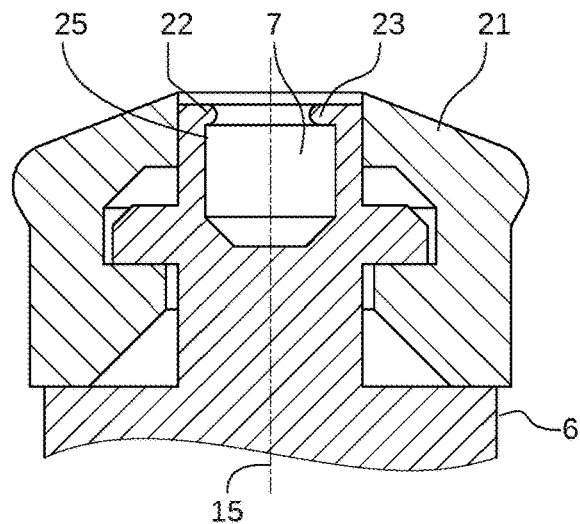
FIG. 6 shows a possible embodiment of the docking system.

FIG. 6 shows a possibility of making the distal part of the piston 6 carrying the docking system capable of cooperating with the tabs of the lower end of the casing 8. The piston 6 has a body provided with a seal 21. The distal end of the body includes a cavity forming the housing 7. This housing 7 is defined, for example, by a wall comprising a bottom and a lateral surface which extends between the bottom and the mouthpiece of the housing 7. Advantageously, a flange protruding laterally towards the longitudinal axis 15 borders this mouthpiece. At this level, the flange is not a symmetrical surface around the longitudinal axis 15. For example, a first area 22 is situated further from the axis 15 than a second area 23. This arrangement is visible in FIG. 6 in cross-section and in top view in FIG. 7. The latter shows that the flange at the mouthpiece of the housing 7 has a large part of a circularly shaped flange at which the area 22 is formed. This portion can therefore be an annular area above the housing 7. The area 23 is advantageously formed so as to protrude further towards the axis 15 relative to the area 22. In general, the area 22 and the area 23 are situated on opposite sides of the axis 15 but are not symmetrical relative to each other with respect to this axis. However, the areas 22, 23 are preferably at the same height and are situated in the same plane perpendicular to the longitudinal axis 15.

Figure 7:
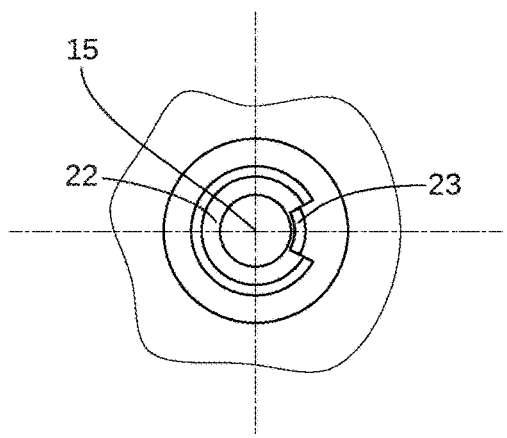
FIG. 7 is a cross-sectional view showing two bearing areas.

FIG. 7 shows that the area 23 can be a section of an annular portion carried by a ring that itself forms the area 22. The angular sector of the area 23 is preferably between 20° and 120°, and advantageously greater than 30° and/or less than 90°.

Figure 8:
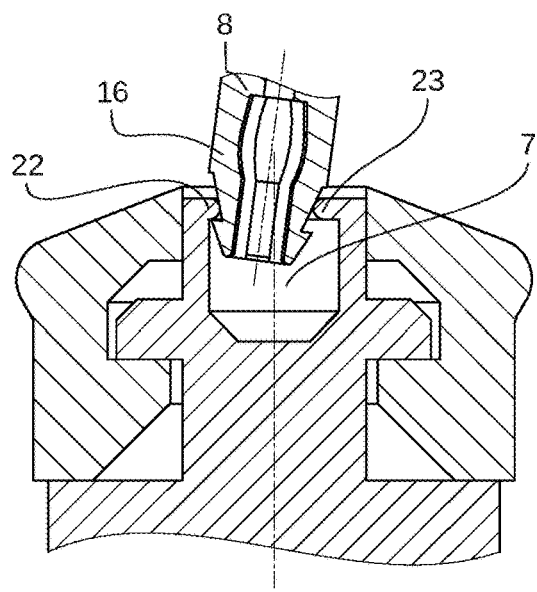
FIG. 8 illustrates an example of the cooperation of parts of the invention in the insertion position.

The interest of the areas 22 and 23 can be understood with reference to FIG. 8 in which the casing 8 is placed in the insertion position in the housing 7. As a matter of fact, a first tab 16 applies to the first bearing area 22 while a second tab 17 applies to the second bearing area 23. Thanks to the flexibility of the tabs, this application is elastic and preferably permanent. The tabs are therefore so configured as to elastically bear simultaneously on the areas 22, 23 in the insertion position. In particular, the distance between the bearing areas 22, 23 shall preferably be smaller than the distance between the surfaces of the latter bearing onto the areas 22, 23, when the tabs 16, 17 are at rest. Because of the asymmetry of the two areas, the forces exerted by the elastic contact of the tabs 16, 17 on these areas are not strictly complementary, which results in the casing 8 being imbalanced and tending to tilt. Preferably, the tabs 16, 17 and possibly 24 only come into contact with the housing 7 at its flange, at the areas 22, 23. In particular, the distal end of the tabs advantageously does not touch the bottom of the housing 7. The positioning of the tabs and the areas 22, 23 is preferably such that it is ensured that at least one of the tabs will come into contact with the area 23 and that at least one other tab will come into contact with the area 22. Thus, preferably, the width of the area 23 is greater than the maximum spacing between two adjacent tabs.

This produces an angular shift between the longitudinal axis of the needle 19 and the longitudinal direction of the rest of the device, in particular of the body 1 and the piston 6. In this way, when the needle 19 is retracted, it shifts laterally to a position equivalent to the one shown in FIG. 2.

REFERENCES

1. Syringe body
2. Cap
3. Interface
4. Head
5. Shoulder
6. Piston
7. Housing
8. Casing
9. Point
10. Flange
11. Slugged bottom
12. Stop
13. Channel
14. Base
15. Longitudinal axis
16. First tab
17. Second tab
18. Stopping area
19. Needle
20. Introduction part
21. Seal
22. First bearing area
23. Second bearing area
24. Additional tab

The invention claimed is:

1. A syringe provided with a body, a piston capable of sliding in the body, and an injection device comprising a needle oriented along a longitudinal axis and a casing removably secured to the body and carrying said needle, the casing comprising a plurality of flexible tabs each provided with a stop, the piston comprising a docking system provided with a housing that comprises a flange configured to hold the stops of the flexible tabs in the housing in an insertion position in which the tabs are inserted into the housing, the plurality of tabs comprising a first tab and a second tab situated in opposing areas around the longitudinal axis, the flange comprising a first bearing area and a second bearing area configured to be in contact with the first tab and the second tab respectively in the insertion position, wherein the first tab and the second tab are configured to provide elastic support respectively on the first bearing area and the second bearing area in the insertion position, and in that the first bearing area and the second bearing area are dissymmetrical relative to the longitudinal axis, wherein a bearing surface of the first bearing area and a bearing surface of the second bearing area extends toward each other at a same height level along the longitudinal axis, and wherein the first bearing area defines a top surface and a bottom surface having a first bearing area height defined there between and the second bearing area defines a top surface and a bottom surface having a second bearing area height defined there between and the first bearing area height and the second bearing area height are the same.

2. A syringe according to claim 1, wherein the first bearing area is further from the longitudinal axis than the second bearing area.

3. A syringe according to claim 2, wherein the first bearing area is on an annular flange and the second bearing area is a portion protruding beyond said flange towards the longitudinal axis.

4. A syringe according to claim 1, wherein the second bearing area is an angular sector of a ring.

5. A syringe according to claim 4, wherein the angular sector forms an angle greater than 30°.

6. A syringe according to claim 4, wherein the angular sector forms an angle of less than 90°.

7. A syringe according to claim 1, wherein a spacing between two adjacent tabs is smaller than a width dimension of the second bearing area.

8. A syringe according to claim 1, wherein the plurality of tabs includes at least one pair of additional flexible tabs, with the tabs of the pair of tabs being situated in opposite areas about the longitudinal axis.

9. A syringe according to claim 8, wherein the first tab, the second tab and the additional flexible tabs are uniformly distributed about the longitudinal axis.

10. A syringe according to claim 8, wherein the plurality of tabs includes only one pair of additional flexible tabs.

11. A syringe according to claim 1, wherein the tabs of the plurality of tabs are symmetrical two by two relative to the longitudinal axis.

12. A syringe according to claim 1, wherein the distal ends of the tabs are disjointed.

\* \* \* \* \*